(12) United States Patent
Humbert et al.

(10) Patent No.: US 8,925,371 B2
(45) Date of Patent: Jan. 6, 2015

(54) SENSOR (75) Inventors: Aurelie Humbert, Brussels (BE); Youri Victorovitch Ponomarev, Leuven (BE); Roel Daamen, Herkenbosch (NL); Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 249 days.

(21) Appl. No.: 13/382,726

(22) PCT Filed: Jul. 16, 2010

(86) PCT No.: PCT/IB2010/053259
§ 371 (c)(1),
(2), (4) Date: Feb. 7, 2012

(87) PCT Pub. No.: WO2011/010264
PCT Pub. Date: Jan. 27, 2011

(65) Prior Publication Data
US 2012/0260732 A1 Oct. 18, 2012

(30) Foreign Application Priority Data
Jul. 21, 2009 (EP) .................... 09290580

(51) Int. Cl.
*G01N 7/00* (2006.01)
*G01N 19/10* (2006.01)
*G01N 27/22* (2006.01)
*G01N 33/00* (2006.01)

(52) U.S. Cl.
CPC ............ *G01N 27/223* (2013.01); *G01N 33/004* (2013.01)
USPC ...... 73/31.05; 73/29.01; 73/335.04; 73/31.01

(58) Field of Classification Search
USPC .......... 73/31.05, 31.01, 31.02, 31.03, 335.05, 73/29.01, 335.04
See application file for complete search history.

(56) References Cited

U.S. PATENT DOCUMENTS

| | | | |
|---|---|---|---|
| 5,021,515 A | 6/1991 | Cochran et al. | |
| 5,841,021 A * | 11/1998 | De Castro et al. | 73/23.2 |
| 6,232,388 B1 | 5/2001 | Lan et al. | |
| 6,486,253 B1 * | 11/2002 | Gilmer et al. | 524/445 |
| 7,176,700 B2 * | 2/2007 | Itakura et al. | 324/689 |
| 2007/0267135 A1 * | 11/2007 | Kim et al. | 156/278 |
| 2010/0000292 A1 * | 1/2010 | Karabacak et al. | 73/24.01 |

FOREIGN PATENT DOCUMENTS

| | | |
|---|---|---|
| CN | 1178903 A | 4/1998 |
| WO | 00/78540 A1 | 12/2000 |
| WO | 2007/036922 A1 | 4/2007 |

OTHER PUBLICATIONS

Korsah, K. et al. "Harmonic Frequency Analysis of SAW Resonator Chemical Sensors: Application to the Detection of Carbon Dioxide and Humidity", Sensors and Actuators B 50, pp. 110-116 (1998).

(Continued)

*Primary Examiner* — Daniel S Larkin
*Assistant Examiner* — Jamar Ray (57) ABSTRACT

A sensor (2) for sensing a first substance and a second substance, the sensor comprising first (3) and second (5) sensor components each comprising a first material (20), the first material being sensitive to both the first substance and the second substance, the sensor further comprising a barrier (18) for preventing the second substance from passing into the second sensor component (5).

14 Claims, 5 Drawing Sheets

(56) References Cited

OTHER PUBLICATIONS

Maul, P. et al. "Barrier Enhancement Using Additives", Pira International Conference, 11 pgs. (Dec. 2005).

Obata, K. et al. "Influences of Water Vapor on NASICON-based $CO_2$ Sensor Operative at Room Temperature", Sensors and Actuators B 93, pp. 243-249 (2003).

International Search Report and Written Opinion for Int'l. Patent Appln. No. PCT/IB2010/053259 (Dec. 2, 2010).

* cited by examiner

SENSOR

This invention relates to a sensor for measuring at least two substances, and particularly, but not exclusively to a sensor for measuring relative humidity and $CO_2$, in the air, or other atmosphere.

It is known to use capacitive or resistive sensors for sensing water vapour and other gases. In a capacitive structure the dielectric constant of the material used to form the structure changes as a function of the substance being measured (e.g. relative humidity or gas concentration). In a resistive sensor, the resistance of the material forming the sensor changes as a function of the substances being measured. By recording changes in the capacitance or resistance respectively, it is possible to monitor levels of, for example, humidity and gas concentration in a particular environment.

There are more and more applications where it is necessary to measure more than one substance at a time. It has therefore previously been necessary to individually integrate sensors into electronic chips to measure, for example, temperature, humidity, gas concentration, pH, optical variables and mechanical variables. In many cases, however, such as the monitoring of perishable goods, it is desirable to have sensors that are able to measure more than one of these substances, or variables to thereby reduce the number of sensors required to measure the variables of interest, or the number of materials used to form the sensors. This enables the cost and complexity of the manufacture of the sensors to be reduced.

A known sensor comprises two Interdigitated electrodes (IDE) coated with a sensitive film. However, a problem with known sensors of this type is that it can be very difficult to measure both moisture content and $CO_2$ concentration using a single sensor. This is because many moisture sensors are also sensitive to $CO_2$ gas, and vice versa.

WO2007/036922 describes a single chip wireless sensor comprising a microcontroller connected to a transmit/receive interface, which is coupled to a wireless antenna by an L-C matching circuit. The sensor senses gas or humidity and temperature. The device is an integrated chip manufactured in a single process in which both the electronics and sensor components are manufactured using standard CMOS processing techniques, applied to achieve both electronic and sensing components in an integrated process. A Low-K material with an organic polymer component is spun onto the wafer to form a top layer incorporating also sensing electrodes. This material is cured at 300 DEG C. The polyimide when cured becomes thermoset, and the lower mass- to-volume ratio resulting in K, its dielectric constant, reducing to 2.9.

WO2000/78540 describes nanocomposites that include a silicate composition and at least one polymer material.

The invention is defined in the accompanying claims.

According to a first aspect of the present invention there is provided a sensor (2) for sensing a first substance and a second substance, the sensor comprising:
first (3) and second (5) sensor components each comprising a first material (20), the first material being sensitive to both the first substance and the second substance; and
a barrier (18) for preventing or reducing the second substance from passing into the second sensor component (5) so that the second sensor component is able to sense levels of the first substance but not the second substance, whereas the first sensor component is able to sense levels of both the first and second substances.

By means of the present invention therefore a sensor is able to measure a first substance and a second substance and it is thus not necessary to have two separate sensors to measure the two substances.

Since the barrier prevents the second substance from penetrating the second sensor component, the second sensor component is able to sense levels of the first substance only, whereas the first sensor component is able to sense levels of both the first and second substances. This means that, from information provided by both the first and second sensor components, it is possible to obtain the values of both the first and second substances in the environment in which the sensor is located.

The first and second substances may comprise $CO_2$ and relative humidity respectively. It can be very useful to be able to measure the concentration of relative humidity and carbon dioxide in an environment in which, for example, perishable goods are stored. By means of the present invention a single sensor may be used to measure both $CO_2$ and moisture content.

The sensor may further comprise a substrate, and the first material may be in the form of a layer extending over a first surface of the substrate.

According to a second aspect of the present invention there is provided a method of forming a sensor (2) for sensing levels of a first substance and a second substance, the method comprising:
depositing a first layer (20) of a first material on a substrate (22), the first layer being formed from a material that is sensitive to both the first substance and the second substance;
forming first (3) and second (5) sensor components from the first material; and depositing a second layer (19) on the first material to form a barrier (18) to prevent or reduce penetration of the second substance into the second sensor component so that the second sensor component is able to sense levels of the first substance but not the second substance, whereas the first sensor component is able to sense levels of both the first and second substances.

In a method according to the second aspect of the invention, the step of forming the first and second sensor components may comprise, prior to the step of depositing the first layer on the substrate, the following steps:
depositing a layer of second material onto the substrate;
patterning and etching the second layer to form a plurality of first electrodes forming part of the first sensor component and a plurality of second electrodes forming part of the second sensor components.

The substrate may be formed from any convenient material such as silicon or silicon dioxide.

The barrier may have any desired thickness, for example, in the region of a few hundreds of nanometers to a few microns.

The barrier may comprise a barrier layer formed from a nanocomposite material. The nanocomposite material may be chosen to act as a barrier to prevent $CO_2$ from passing into the second sensor component. In particular, the nanocomposite material may prevent diffusion of $CO_2$ into the second capacitor.

The nanocomposite material may comprise a nanoclay inserted into a polymer matrix.

The polymer matrix may be any suitable polymer matrix such as a polyamide, particularly metaxylylene adipamide. Because the nanocomposite material is inserted into a polymer matrix, the orientation of the nanocomposite particles may be controlled to provide appropriate barrier properties.

The barrier may completely surround the second sensor component. Alternatively, the barrier may further comprise a pillar. The pillar may extend through the first material, and in embodiments of the invention comprising a substrate, the pillar may extend from a first surface of the substrate substantially perpendicularly to the first surface. The pillar therefore acts with the barrier layer to separate the first sensor component from the second sensor component. Such an arrangement facilitates the manufacture of the sensor.

The first sensor component may comprise a first capacitor having a first dielectric formed from the first material, and the second sensor component may comprise a second capacitor having a second dielectric formed from the first material.

In such an embodiment of the invention, the capacitance of the first capacitor will be proportional to the levels of both the first substance and the second substance in the environment in which the sensor is positioned, whereas the capacitance of the second capacitor will be proportional to the levels of the second component only.

The first material comprise any suitable material such as polyimides, $Al_2O_3$, $TiO_2$, $SiO_2$, $S_iC$, polyesters, PMMA (Polymethyl methacrylate), BCB (Benzocyclobutene), polysulfates, cellulose acetate butyrate, porous silicon, polysiloxanes, polysilazanes, Fluoropolymer, CuO mixed with $BaSnO_3$, $SrTiO_3$, $CaTiO_3$, ZnO or $BaTiO_3$, $SnO_2$ based film etc.

In another embodiment of the invention, the first and second sensor components may comprise first and second resistors respectively. In such an embodiment, the first material comprises a resistive material which forms both the first and second resistors.

Suitable resistive materials may be metal oxides, such as La2O3, TiO2, SrtiO2, SnO2, ZnO, LaMnO3, BaZrO3, BaSnO3, WO3, In2O3, Nb2O5, CeO2, ZrO2, Ga2O3, perovskite-like oxides. These metal oxides may be doped or undoped.

Polymer materials having resistive properties such as polypyrrole and polyaniline may also be used.

The first material may have any desired thickness, but preferably has a thickness in the range from 0.5 to 10 microns. The thickness of the first material may be in the order of 2 to 3 microns.

The first sensor component may comprise a plurality of first electrodes embedded in the first material, and the second capacitor may comprise a second plurality of second electrodes buried in the second material.

The first electrodes, second electrodes and pillar may be formed from the same material.

The material used to form the electrodes and pillar may be any convenient metal such as aluminium (Al), titanium (Ti), tungsten (W), cobalt (Co), nickel (Ni), Tantalum (Ta), or copper (Cu). If any of these metals is used to form the electrodes, then standard CMOS processing techniques may be used. Alternatively any of the following metals may be used: platinum, gold, iron, zinc, chromium, magnesium, protactinium, silver, tin, indium.

The electrodes may have any suitable thickness but preferably the height of each of the first, second and pillar electrode is in the range 50 nm to a few microns. Each electrode will have a height in the range of 400 to 800 nm, for example.

The sensor may further comprise a heater for heating the sensor. This can be particularly advantageous in situations where a high operational temperature is needed in order to obtain appropriate information on the first and second substances to be measured.

In embodiments of the invention comprising a substrate, the heater may be formed in the substrate.

The heater may take the form of a metal layer embedded in the substrate through which a current may be passed. By passing a current through the metal, heat will be generated.

The sensor may be fabricated by any suitable fabrication method. Preferably however CMOS processing fabrication steps may be used. This is particularly the case when the electrodes are formed from a metal which is compatible with such processes. The sensor may thus be formed by depositing layers of material onto a substrate, or other layer.

The first material may be deposited onto the substrate formed from, for example, silicon, silicon dioxide, or metal.

Any known deposition techniques such as CVD (Chemical Vapour Deposition), PECVD (Plasma Enhanced Chemical Vapour Deposition), ALD (Atomic Layer Deposition) or sputtering can be used. The layers may be patterned to form appropriate shapes using any known patterning techniques such as optical lithography, UV lithography, electron beam lithography. Once patterning has taken place, known etching techniques such as dry etching, wet etching, vapour etching may be used to form components having appropriate dimensions.

The barrier layer may be deposited using any of the deposition techniques mentioned above, or may be deposited using injection moulding, blow moulding, or film casting as long as all the components forming the sensor are adapted to withstand the temperatures required for using such processes.

Inkjet printing techniques may also be used. If inkjet printing techniques are used, the barrier can be applied using inkjet printing whereby the barrier is printed onto a flexible film which may be positioned over the second sensor component after the first and second sensor components have been fabricated.

Alternatively, the entire sensor may be fabricated using inkjet printing techniques.

A sensor according to embodiments of the invention may be integrated on to CMOS circuitry.

A sensor according to embodiments of the invention may thus form part of a much larger overall structure comprising several layers positioned generally below the sensor.

A sensor according to embodiments of the present invention has applications in radio frequency identification and may be in the form of a CMOS sensor.

By means of the present invention therefore a small low cost, low powered RFID chip may be produced.

The embodiments invention will now be further described by way of example only in which.

Figure 1:
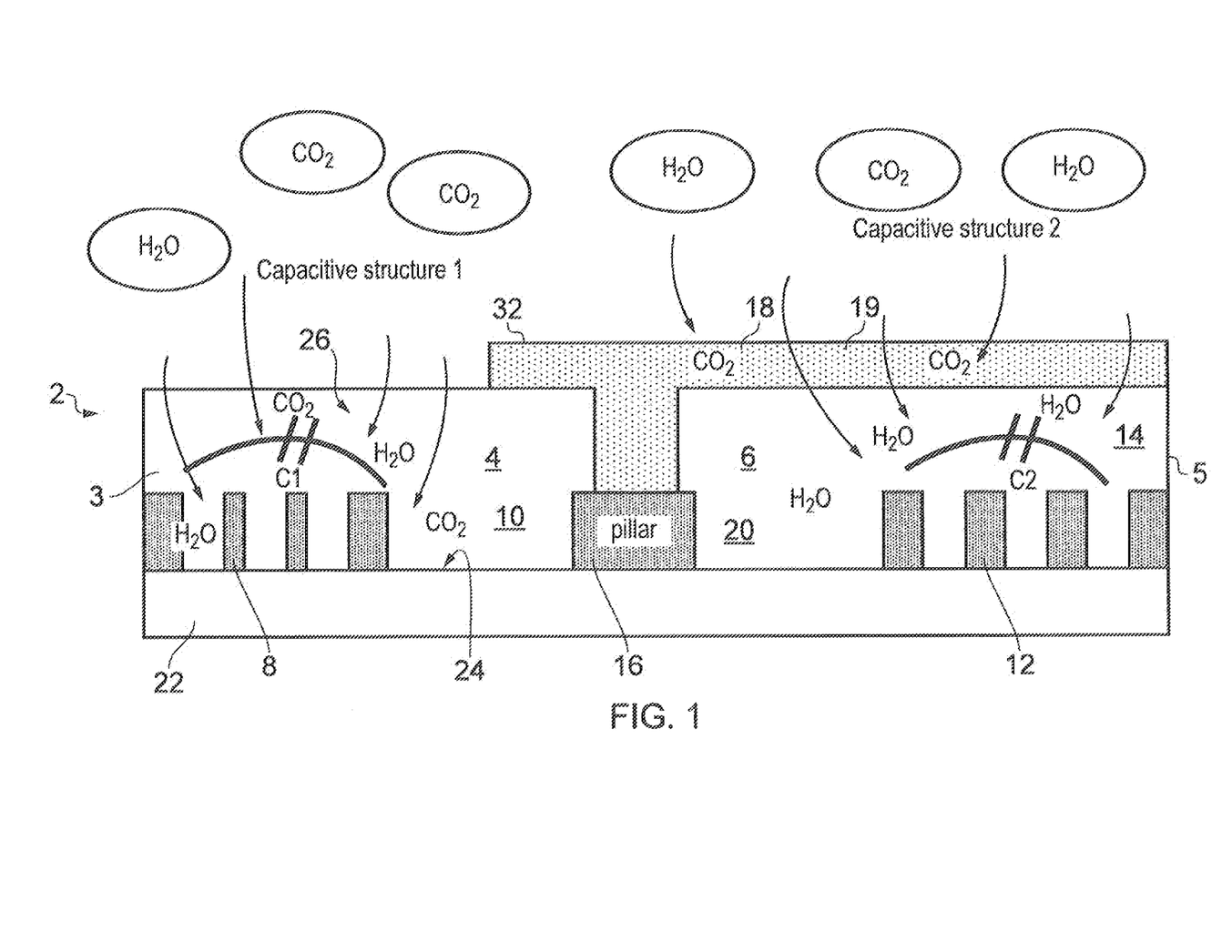
FIG. 1 is a schematic representation of a sensor according to a first embodiment of the present invention.

Referring initially to FIG. 1, a sensor according to an embodiment of a first aspect of the invention is designated generally by the reference number 2.

The sensor 2 comprises a first sensor component 3 comprising a first capacitor 4 and a second sensor component 5 comprising a second capacitor 6. The first capacitor 4 comprises a plurality of first electrodes 8 embedded in a first dielectric 10 formed from a layer 20 of first material. The second capacitor 6 comprises a plurality of second electrodes 12 embedded in a second dielectric 14 also formed from the first material.

Each of the capacitors 4, 6 is formed from the first material which in this example comprises silicon dioxide ($SiO_2$).

The first material is formed on a surface 24 of substrate 22 and comprises a surface 26.

The first and second electrodes 8, 12 are each formed from any convenient metal such as aluminium.

Typically, the thickness of the electrodes will be within the range of a few microns to about 50 nanometres and preferably will be in the range of 400-800 nanometres.

The thickness of each dielectric 10, 14 is between 0.5 and 10 microns. Typically the thickness of each dielectric is 2-3 microns.

The sensor comprises a barrier 18 covering the second capacitor 6. The barrier is formed from a barrier layer 19 formed from a nanocomposite layer that acts as a barrier and prevents $CO_2$ diffusion into the second capacitor 6. The barrier layer 19 is preferably formed from a nanocomposite layer comprising a nanoclay inserted into a polymer matrix.

Such nanocomposites are known to be able to act as barriers to many gases due to the structure of the nanoclay. A nanoclay is a type of clay mineral having a specialised structure characterised by a platey morphology. The platelets have submicron dimensions, apart from the thickness, which is about 1 nm. The dimensional disparity between the thickness of platelets and the other dimensions of the platelets results in a large aspect ratio. This property is conducive to barrier enhancements since platelets of this shape arrange themselves to create a tortuous migration path. When a nanoclay is inserted into a polymer matrix, the relative orientation of the platelets is maintained. Because the nanoclay is inserted into a polymer matrix, it is possible to ensure that the orientation of the platelets of the nanoclay is such that the appropriate barrier properties are achieved.

The barrier 18 further comprises a pillar 16 made from the same material as that of the first and second electrodes 8, 12. The pillar extends from surface 24 of the substrate 22 and into the layer 20 of first material. On the other hand, the nanocomposite layer 19 extends from surface 26 of the first material to the pillar 16. The nanocomposite layer 19 and the pillar 16 together thus form barrier 18 and prevents or reduce $CO_2$ diffusion into the second capacitor 6. The pillar thus acts as a lateral barrier against $CO_2$ The resulting sensor 2 is able to measure both moisture content (relative humidity) and $CO_2$ content in the environment in which it is positioned. This is because the material forming each of the first and second dielectrics 10, 14 is sensitive to both $CO_2$ and water. However, the presence of barrier 18 means that little, if any, $CO_2$ is able to penetrate through the barrier 18 and thus does not reach the second capacitor 6.

The second capacitor 6 is thus sensitive to the moisture content only (since no $CO_2$, or very little $CO_2$, will reach the capacitor 6), whereas the first capacitor 4 remains sensitive to both moisture and $CO_2$.

The capacitance C1 of the first capacitor 4, will therefore be proportional to the levels of both water and $CO_2$ in the environment, whereas the capacitance, C2, of the second capacitor 6 will be proportional to the levels of water only in the environment. It is thus possible to obtain concentrations of both carbon dioxide and water in the environment from C1 and C2.

The sensor illustrated in FIG. 1 may be manufactured using known deposition techniques such as CVD (Chemical Vapour Deposition), PECVD (Plasma Enhanced Chemical Vapour Deposition), ALD (Atomic Layer Deposition), or sputtering, for example.

Figure 2:
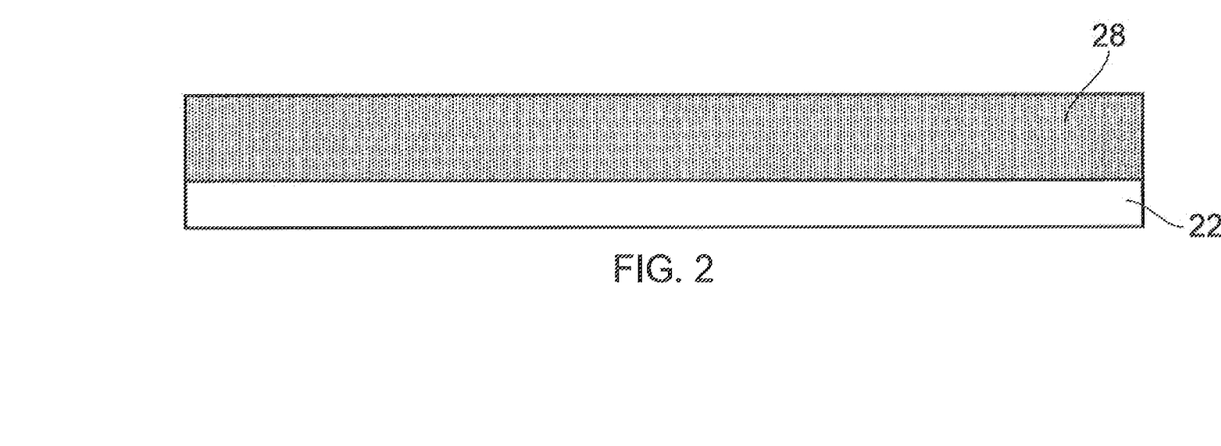
FIGS. 2 to 6 are schematic representations showing how the sensor of FIG. 1 may be fabricated.

The first step as shown in FIG. 2 is that layer 28 of material that will form the electrodes 8, 12 and pillar 16 is initially deposited on a silicon substrate 22. In this example, layer 28 is formed from aluminium, and has a thickness of between 400 and 800 nm.

Figure 3:
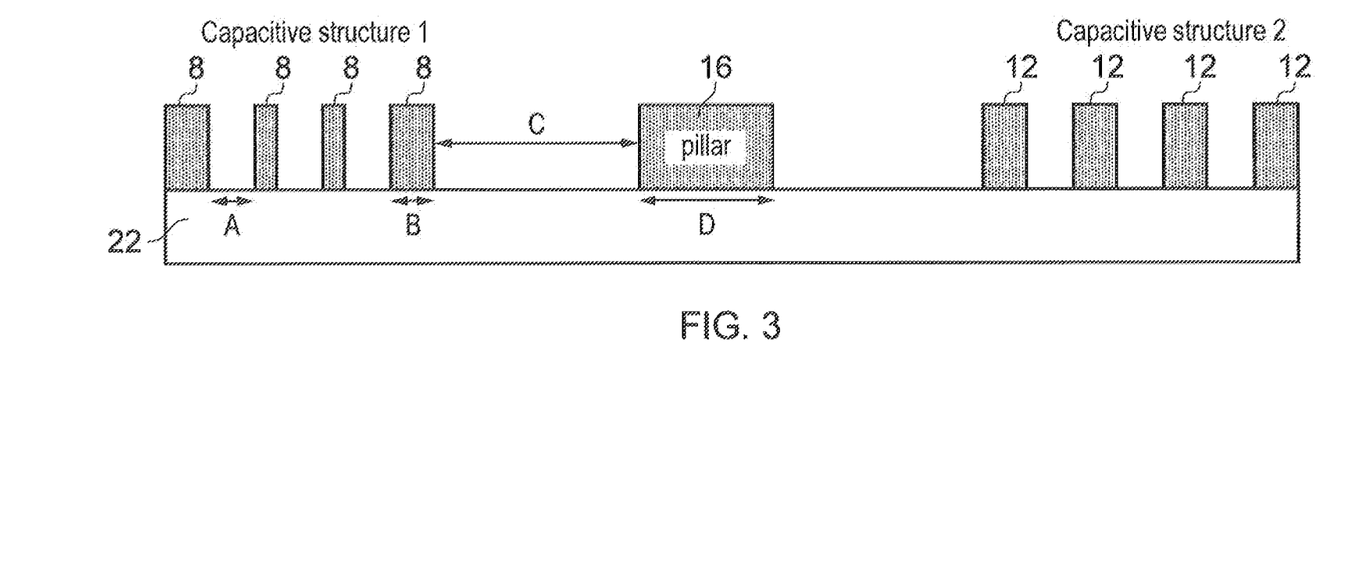

As shown in FIG. 3, the next step is the patterning of the electrodes 8, 12 and pillar 16. Any known technique may be used such as optical lithography, UV lithography, electron beam lithography for example. Once patterned, the layer 28 may be etched using techniques such as dry etching, wet etching, vapour etching, etc, to form the desired electrode structure.

Typically, the distance between adjacent electrodes 8, 12 (distance A) will be about 500 nm. The thickness of each electrode 8, 12 (distance B) will also be about 500 nm.

The distance between the pillar 16 and the nearest electrode 8 or 12 (distance C) is in the order of 5 microns. This is to remove or reduce any parasitic capacitance from the pillar electrode and either of the adjacent electrodes.

The pillar itself must be large enough to allow the patterning and the deposition of further layers on top of the pillar and in this example will be of the order of 2 microns wide (distance D).

If metals such as copper and tungsten are used, a different type of integration can be used known as damascene integration. In this case, the deposition of the metal is carried out after the creation of holes in the dielectric layer. Such a method is not a direct patterning method. This means for metals such as copper and tungsten, deposition of the first material must initially be carried out. This layer is then patterned and etched to form holes for the electrodes and pillar. Next metal is deposited into these holes to form the electrodes and pillar. The metal is then subjected to chemical mechanical planarization. Next, the barrier is deposited as described hereinabove.

Figure 4:
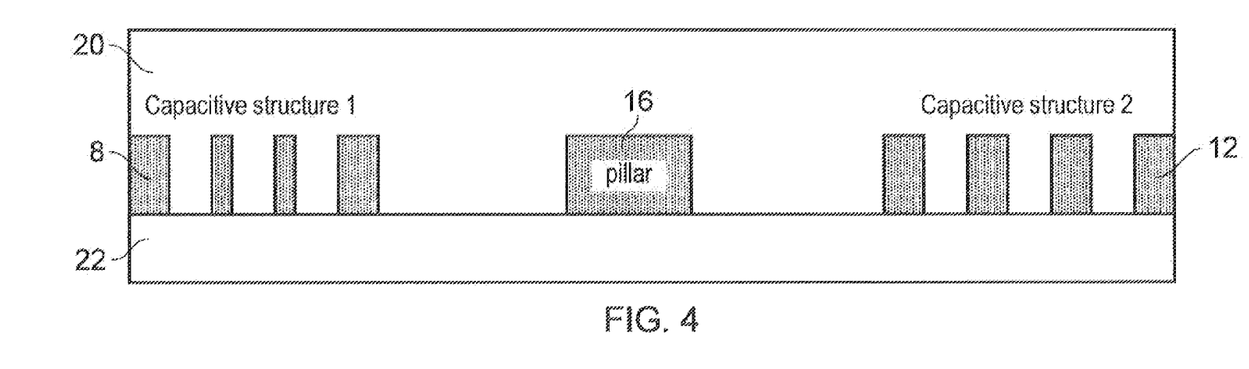

Turning now to FIG. 4, layer 20 which in this embodiment comprises a dielectric material is next deposited over the electrodes 8, 12, and pillar 16 using known techniques such as CVD, PECVD, ALD, sputtering or spin coating, sol-gel processing, for example. In this example layer 20 comprises a polyimide.

Figure 5:
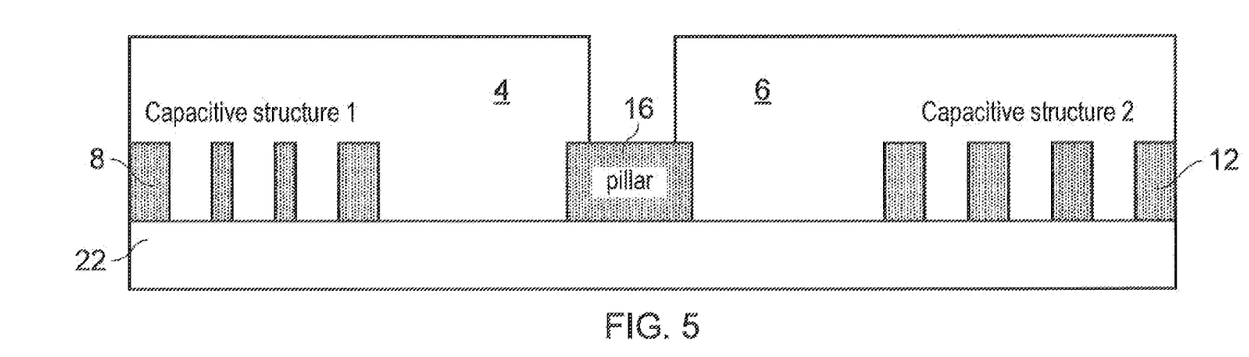
Figure 6:
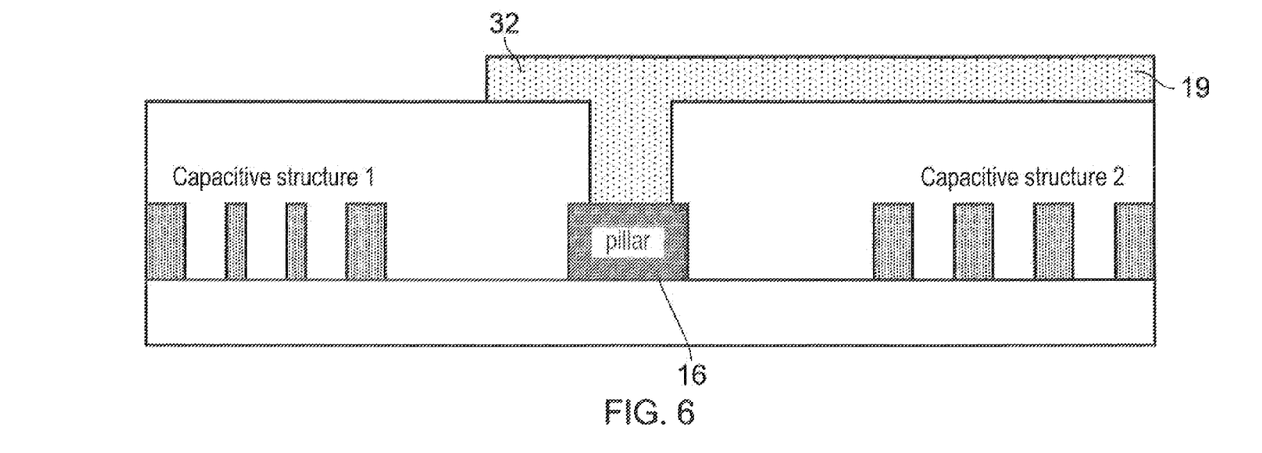

Next, the layer 20 must be etched as shown in FIG. 5 using conventional techniques of the type described hereinabove with reference to FIG. 3.

Finally, the barrier layer 19 is deposited over the dielectric layer 20 and is also patterned using known techniques to form the sensor 2 as shown in FIG. 1. In this example the layer 19 comprises a nanocomposite comprising a nanoclay inserted into a polymer matrix, although other materials could be used.

As shown in FIG. 1, the layer 19 comprises a portion 32 that extends beyond the capacitor 6 and overlies the first capacitor 4.

It is not necessary for the barrier layer 19 to extend over the first capacitor 4 in this way. However, the extension portion 32 means that if there is any misalignment that occurs during the fabrication process, it should still be possible to ensure that the barrier layer 19 connects with the pillar 16 to form barrier 18, thus preventing lateral diffusion of $CO_2$ from the first capacitor 4 into the second capacitor 6.

Figure 7:
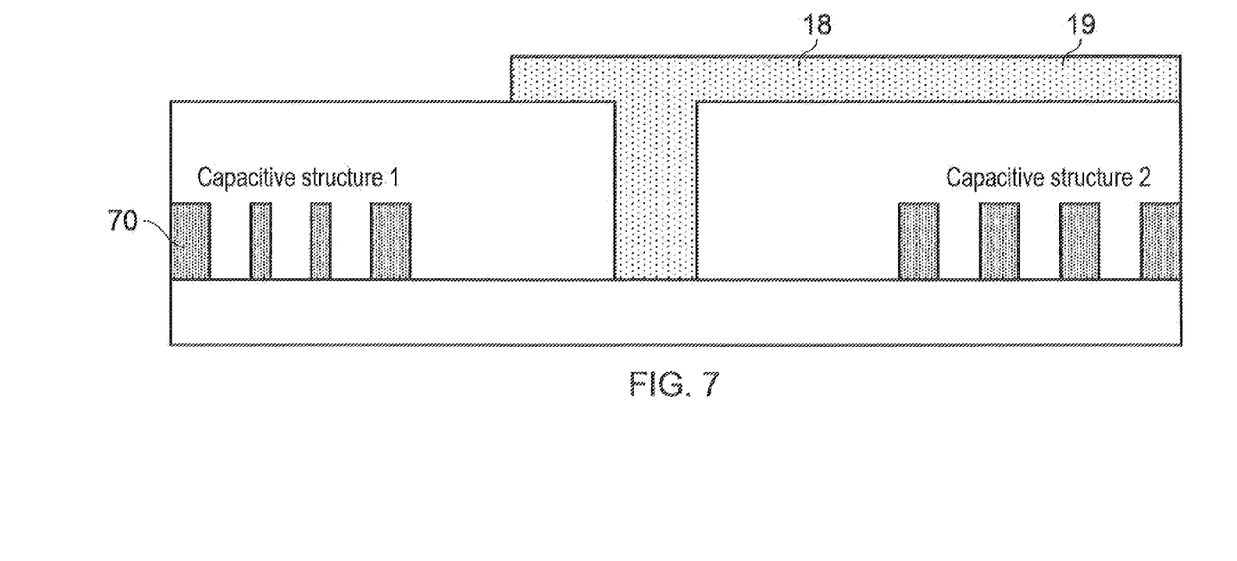
FIG. 7 is a schematic representation of a sensor according to a second embodiment of the invention.

Turning now to FIG. 7, a sensor according to a second embodiment of the invention is designated generally by the reference numeral 70. Parts of the sensor 70 that correspond to parts of the sensor 2 have been given corresponding reference numerals for ease of reference.

Sensor 70 differs from sensor 2 in that there is no pillar 16 in the sensor 70. Instead, the barrier layer 19 extends through the layer 20 of first material to the substrate 22. It is thus not necessary to have a pillar 16 present in order to ensure that there is a barrier between the first capacitor 4 and the second capacitor 6. In order to fabricate such a sensor, it is necessary to etch the dielectric layer 20 and then to deposit the barrier layer 19 into the thus formed trench.

Figure 8:
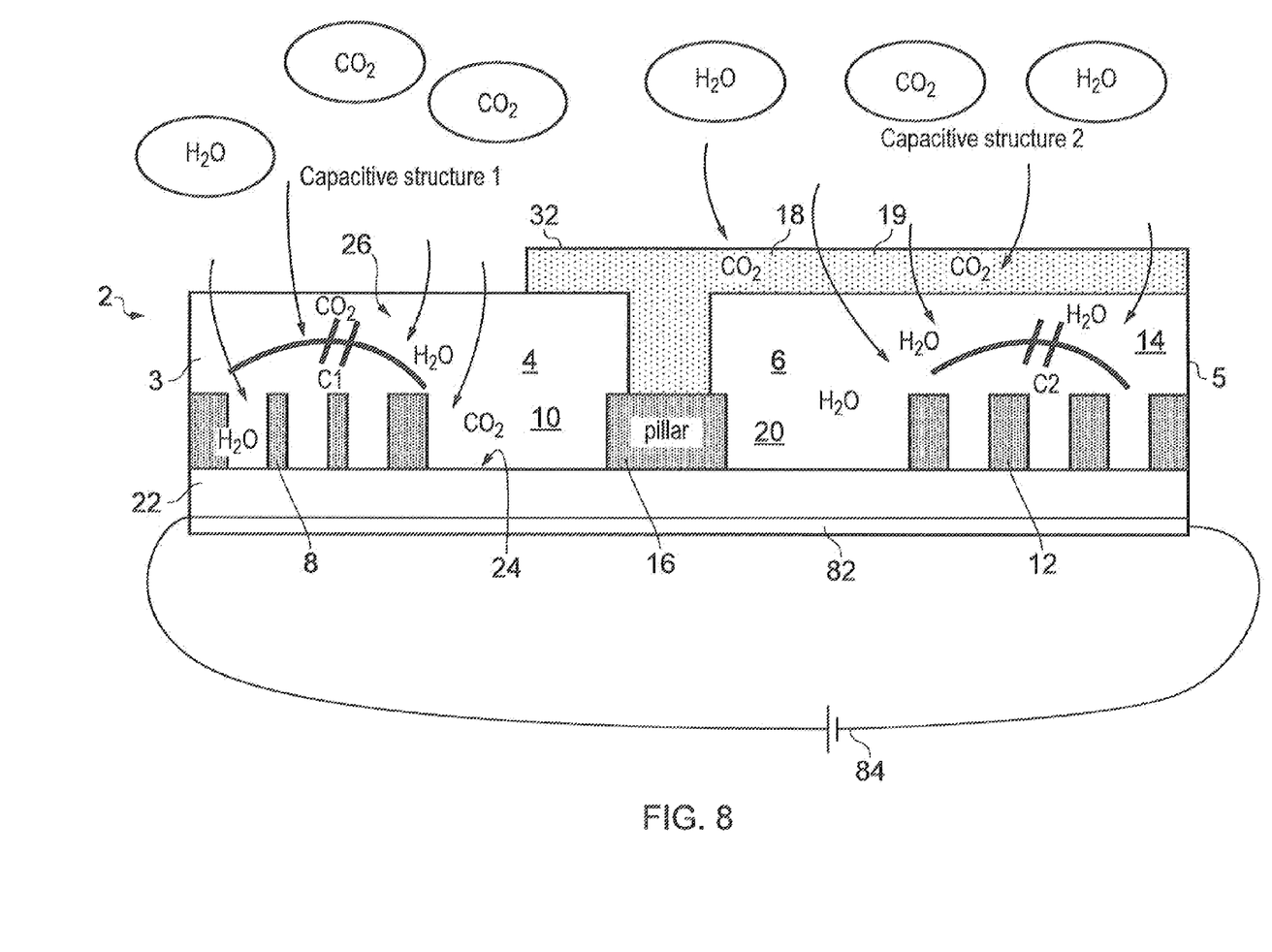
FIG. 8 is a schematic representation of a sensor according to a third embodiment of the invention.

Referring now to FIG. 8, a sensor according to a third embodiment of the invention is designated generally by the reference numeral 80. Parts of the sensor 80 that correspond to parts of the sensors 2, 70 have been given corresponding reference numerals for ease of reference.

Sensor 80 further comprises a metal layer 82 formed in the substrate 22. The sensor further comprises means 84 for applying a current through the layer 82. The application of a current through the layer 82 causes the layer to heat up thus heating the sensor.

Although the sensors 2, 70, 80 have been described with reference to first and second sensor components comprising capacitors, such sensors could also comprise first and second sensor components in the form of resistors. In such sensors, the first material would be formed from a resistive material rather than a dielectric material.

The invention claimed is:

1. A sensor for sensing a first substance and a second substance, the sensor comprising:
    first and second sensor components each comprising a first material, the first material being sensitive to both the first substance and the second substance; and
    a barrier for at least reducing penetration of the second substance into the second sensor component so that the second sensor component is able to sense levels of the first substance and not the second substance, whereas the first sensor component is able to sense levels of both the first and the second substances; and
    wherein the barrier further comprises a pillar extending through the first material.

2. A sensor according to claim 1 further comprising a substrate, wherein the first material comprises a layer extending over a first surface of the substrate.

3. A sensor according to claim 1 wherein the barrier comprises a barrier layer formed from a nanocomposite material.

4. A sensor according to claim 3 wherein the nanocomposite material comprises a nanoclay inserted into a polymer matrix.

5. A sensor according to claim 4 wherein the polymer matrix comprises a polyimide.

6. A sensor according to claim 1 wherein the first sensor component comprises a first capacitor having a first dielectric formed from the first material, and the second sensor component comprises a second capacitor having a second dielectric formed from the first material.

7. A sensor according to claim 1, wherein the first sensor component comprises a first resistor, the second sensor component comprises a second resistor, and the first material comprises a resistive material.

8. A sensor according to claim 1 wherein the first sensor component comprises a plurality of first electrodes embedded in the first material.

9. A sensor according claim 8 wherein the second sensor component comprises a plurality of second electrodes embedded in the second material.

10. A sensor according to claim 9 wherein the first and second electrodes are formed from aluminum.

11. A sensor according to claim 1 further comprising a heater.

12. A sensor according to claim 11, wherein the heater comprises a layer embedded in the substrate.

13. A method of forming a sensor for sensing levels of a first substance and a second substance, the method comprising:
    depositing a first layer of a first material on a substrate, the first layer being formed from a material that is sensitive to both the first substance and the second substance;
    forming first and second sensor components from the first material; and
    depositing a second layer on the first material to form a barrier to at least reduce penetration of the second substance into the second sensor component so that the second sensor component is able to sense levels of the first substance but not the second substance, whereas the first sensor component is able to sense levels of both the first and second substances; and
    wherein the step of forming the first and second sensor components comprises, prior to the step of depositing the first layer on the substrate:
    depositing a layer of second material onto the substrate; and
    patterning and etching the second layer to form a plurality of first electrodes forming part of the first sensor component and a plurality of second electrodes forming part of the second sensor components.

14. A method according claim 13 wherein the first sensor component comprises a first capacitor having a first dielectric formed from the first material, and the second sensor component comprises a second capacitor having a second dielectric formed from the first material.

\* \* \* \* \*